United States Patent [19]
Nordin et al.

[11] Patent Number: 5,384,857
[45] Date of Patent: Jan. 24, 1995

[54] SNAP-IN ATTACHMENT FOR EAR DEFENDER CUP

[75] Inventors: Henrik Nordin, Forsheda; Sigvard Nilsson, Gnosjo, both of Sweden

[73] Assignee: Peltor Aktienbolag, Varnamo, Sweden

[21] Appl. No.: 143,290

[22] Filed: Oct. 26, 1993

[30] Foreign Application Priority Data

Oct. 29, 1992 [SE] Sweden .............................. 9203209-3

[51] Int. Cl.⁶ .................... H04R 25/00; F16B 7/10; B25G 3/00
[52] U.S. Cl. ................................... 381/183; 381/187; 403/383; 403/106
[58] Field of Search .............. 381/183, 187; 248/213.1, 222.1, 222.2, 222.3; 379/430, 455, 454; 403/383, 106, 103, 104, 83

[56] References Cited

U.S. PATENT DOCUMENTS

| | | |
|---|---|---|
| 2,383,068 | 8/1945 | MacLean, Jr. .................. 248/222.4 |
| 5,185,807 | 2/1993 | Bergin et al. ...................... 381/183 |

Primary Examiner—Curtis Kuntz
Assistant Examiner—Sinh Tran
Attorney, Agent, or Firm—Ostrolenk, Faber, Gerb & Soffen

[57] ABSTRACT

A snap-in attachment of a headband or other support means for a hearing-protection cup is described. The snap-in contact comprises a sliding pin (6) the journal section (7) of which is oval or elliptical in cross section, and a jaw element with two resiliently deformable jaws (11, 12). The inner walls (21, 22) of the jaws (11, 12) and the wall section (20) connecting them define a locking space (13). The journal section (7) of the sliding pin can be inserted into the locking space (13) against a resilient counter member only in the direction of the longitudinal axis of the journal section (7) and is thus lockable between the jaws (11, 12) in a first locked position. After being turned (angle α) against another resilient counter member, the sliding pin is locked by its journal section (7) in the locking space (13) in a second locked position, in which it is pivotable to a limited extent (sector with angle β).

20 Claims, 3 Drawing Sheets

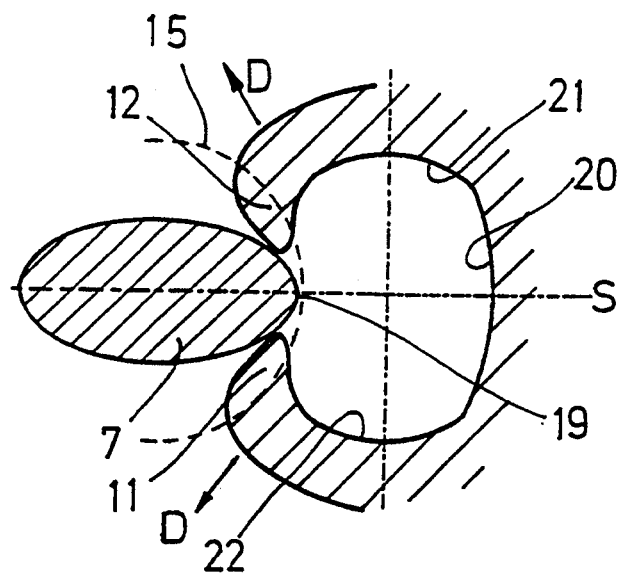
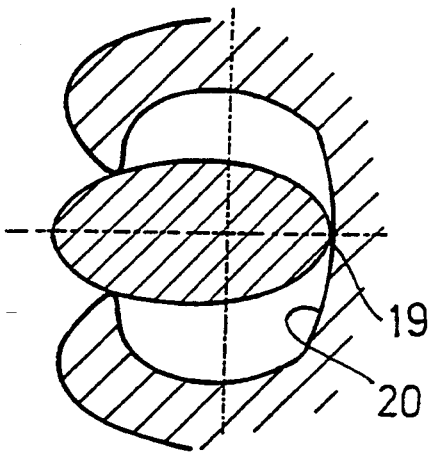
FIG.6a  FIG.6b
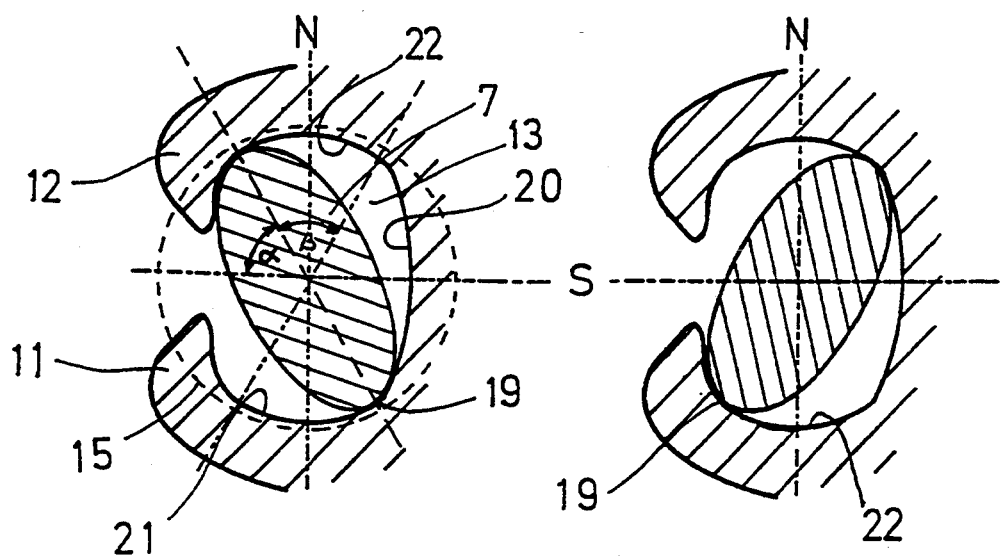
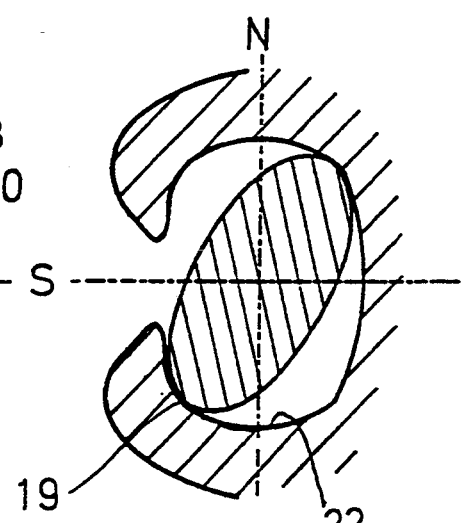
FIG.6c  FIG.6d

SNAP-IN ATTACHMENT FOR EAR DEFENDER CUP

FIELD OF THE INVENTION

The present invention relates to a detachable snap-in attachment of a headband or other support means for ear defender cups or the like which, when in place, are pivotable in relation to the headband. The snap-in attachment comprises at least one, preferably two, sliding pins arranged in line with each other on opposite lateral sides of the ear defender cup perpendicular to the respective side, and is provided with stop flanges at the ends facing away from each other, so that when in place each sliding pin is held pivotably between two jaws in one each of two mutually parallel jaw elements symmetrically in relation to the sliding pins at each end of the headband.

The term ear defenders in this application relates to hearing-protection means for suppressing noise, particularly noise during work, comprising (a) two noise-suppressing cups designed to cover the ears sealingly thereby enclosing them in the cups and excluding undesired noise, and (b) means for securing the cups against the ears, such as a headband or neckband or short separate yokes or the like, for instance secured in a helmet or the like. The cups may be provided with additional equipment such as a headphone.

PRIOR ART

In order to satisfy individual variations in head shape, the cups are usually pivotably attached to the head band, the attachment generally being such as to permit oscillation of the cups in the plane of the headband. To ensure good stability with minimum weight, the band is divided into two arms at the cups and the cup is pivotably attached on its opposite short sides by means of hinges, i.e. two-point suspension. To enable exchange of the cups the attachment is usually detachable and the positioning means is usually some form of snap-in mechanism. Depending on the construction of the snap-in mechanism the cup is snapped in either in the direction of its pivot axis or perpendicular thereto.

There is room for improvement in the known snap-in means for pivotable attachment of ear defender cups to a headband or the like. For instance, the built-in pivot function allows the cup to pivot through a large angle about the axis and to assume almost any position in relation to each other and the headband. To enable easy application of the ear defenders it is important that the cups automatically assume a position in which their contact surfaces against the head do not deviate very much from the position in which they were applied, in which position the contact surfaces are approximately parallel. Application is made more difficult if, as implied above, the cups are not forced to assume this position in relation to each other. Both hands are needed to turn the cups to the correct position during application, and this is a drawback in many work situations when one hand is required for other tasks.

The known snap-in mechanisms, usually made of plastic and are subject to wear since the cup must be placed on the headband or removed from it; considerable force is often required to effect these procedures.

OBJECTS OF THE INVENTION

It is a principal object of the present invention to provide a snap-in attachment of the type described in the introduction, which does not have these drawbacks, which is as easy to manufacture as the known snap-in attachments, and which is also advantageous in other respects.

SUMMARY OF THE INVENTION

According to the present invention a detachable snap-in attachment is defined in which the sliding pins have double mirror-image symmetry in a plane perpendicular to their axes of rotation, the sliding pins being preferably oval or elliptical in their journal section and, to effect attachment, are able to be inserted into the gap between the jaws only in the direction of the longitudinal axes of the journal section.

It is preferred that when in place the sliding pins are freely pivotable in relation to the headband within a sector where the sector angle $\beta$ is between approximately 20° and approximately 80°, preferably approximately 55°.

It is also preferred that when in place the sliding pins are freely pivotable in relation to the headband within an angular range, relative to the direction of insertion of the sliding pin in the gap between the jaws, of from between approximately 50° and approximately 130° to between approximately 80° and approximately 100°, preferably between approximately 62.5° and 107.5°.

When in place the sliding pins are preferably lockable in the jaws either in or against the direction of insertion.

According to a preferred aspect of the invention the eccentricity, i.e. the ratio between the length of the short axis of the journal section and its longitudinal axis, is between approximately 1:1.3 and approximately 1:5, preferably approximately 1:2.

According to another preferred aspect of the invention the inner walls of the gap and the jaws, and the wall section connecting the inner walls of the jaws define a locking space, the length of the longitudinal axis of the oval or ellipse defining the sliding pin being equal to or negligibly smaller than the diameter of a circle defining the curvature of the first wall section of the inner wall of the locking space which, calculated from the direction of insertion of the sliding pin, extends at a positive or negative angle from at most between approximately 40° and approximately 140° to at least between approximately 75° and approximately 105°, preferably between approximately 60° and 120°.

According to a third preferred aspect of the invention the curvature of the second wall section of the inner wall of the locking space, shaped substantially as a segment of a circle and facing the insertion opening, is defined by a radius considerably larger than the radius of curvature of the circular-segment shaped first wall sections, the substantially circular-segment shaped second wall section extending in a sector the sector angle of which is substantially determined by the sector angles of the substantially circular segment shaped first wall sections. The radius defining the curvature of the substantially circular-segment shaped second wall section facing the insertion opening is then approximately twice the radius of the substantially circular segment shaped first wall section.

The sliding pin and thus the ear defender cup or ear-muff are thereby able to assume two positions when in place. One of these positions, the operative position, is that in which the ear-muff is freely movable within a limited sector about the vertical (defined as the position of the cup when the ear-muff is worn by a person standing upright). In the other position, the inspection position, when the cup openings face away from the headband, the contact openings are in a plane allowing for easy access for inspection, replacing the hygiene insert or the like, without the cups having to be dismantled. Furthermore, the ear-muffs can also be conveniently stored in upright position on a flat surface against which the sealing contact surfaces of the cups rest, the interior of the cups thereby being protected from dust and the like if they are to be stored for an extended period.

According to the invention the journal section of the sliding pin is partially insertable and lockable in the jaws against a first resilient counter member and lockable in the locking space by being turned towards a second resilient counter member.

Suitably the surfaces of the jaws able to abut the sliding pin, and the surfaces of the sliding pin able to abut the jaws are shaped congruently, preferably perpendicular to the plane of the jaws or parallel to this plane.

The invention also defines an ear defender cup, an ear defender, and a noise-suppressed headset having one or more snap-in attachments according to the invention.

The invention also defines a jaw socket movable on a headband or similar support means, for assembly of an ear defender cup, a noise-suppressed headphone or the like, said jaw socket forming part of a snap-in attachment according to the invention.

BRIEF DESCRIPTION OF THE DRAWINGS

The invention will be described in more detail in the following with reference to the accompanying drawings relating to a preferred but not limiting embodiment.

FIG. 6a–6a are diagrammatic sketches illustrating assembly of the snap-in member and its two stable positions when in place.

DETAILED DESCRIPTION OF A PREFERRED EMBODIMENT

Figure 1:
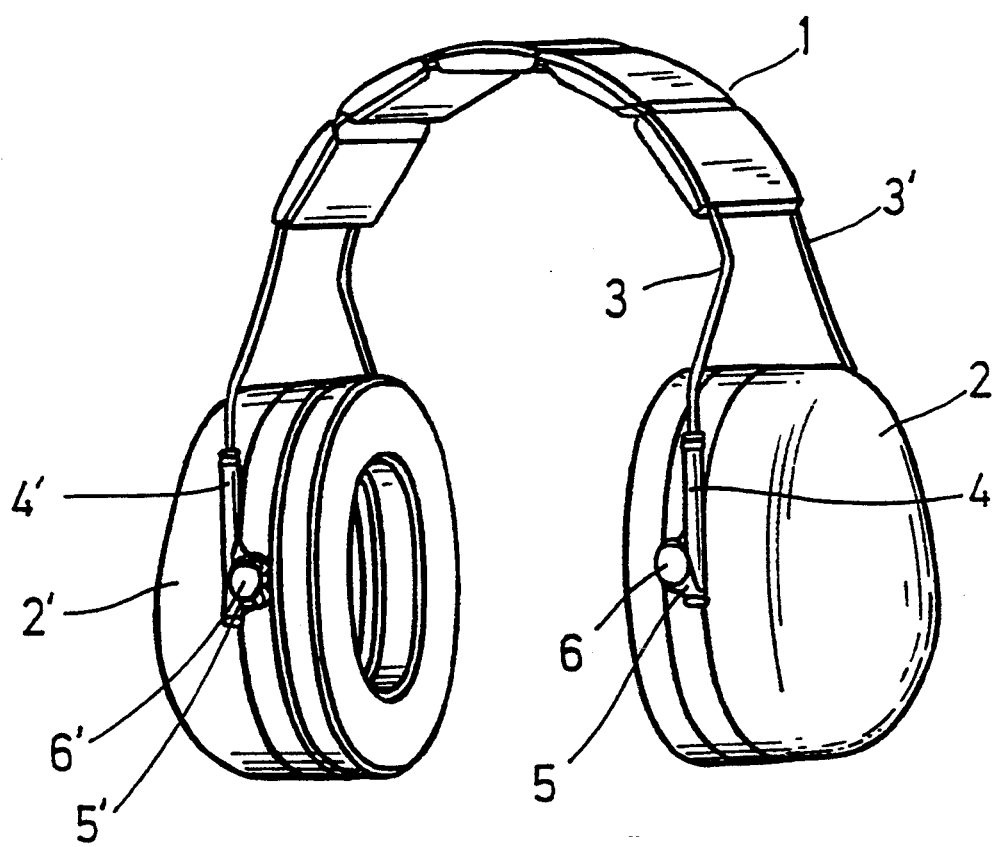
FIG. 1 shows in perspective an ear defender with two hearing-protection cups provided with detachable snap-in attachments according to the invention on a reduced scale.
Figure 5:
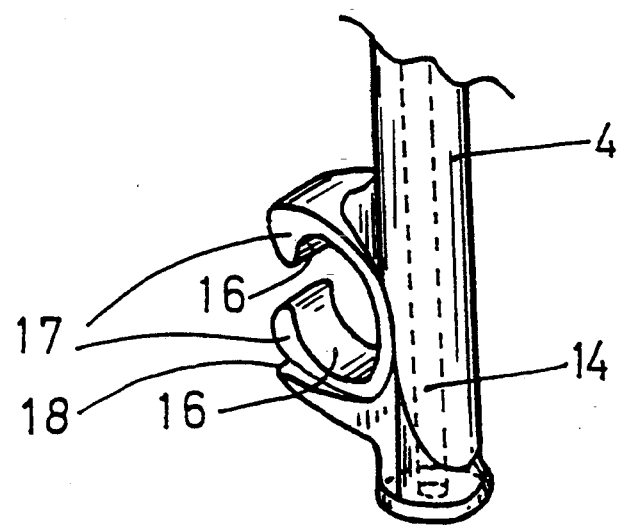
FIG. 5 shows a partial view of the jaw member in FIG. 4 in perspective.

The ear-muff shown in FIG. 1 comprises a headband 1 and two oval, shell-shaped ear defender cups 2, 2'. The headband 1 consists of a pair of frames 3, 3' made cut of stainless steel, located parallel to each other and secured by curing of the central parts in flexible plastic strips. After leaving the area where they are embedded in plastic the frames bend apart on each side of the central section of the headband and, after another bend closer to their ends they again become parallel to each other. The end sections of the frames 3, 3' at each end of the headband is slidably fitted in jaw sockets, only one of these sockets 4 being shown in FIG. 1; the equivalent is applicable to the other end section.

Figure 2:
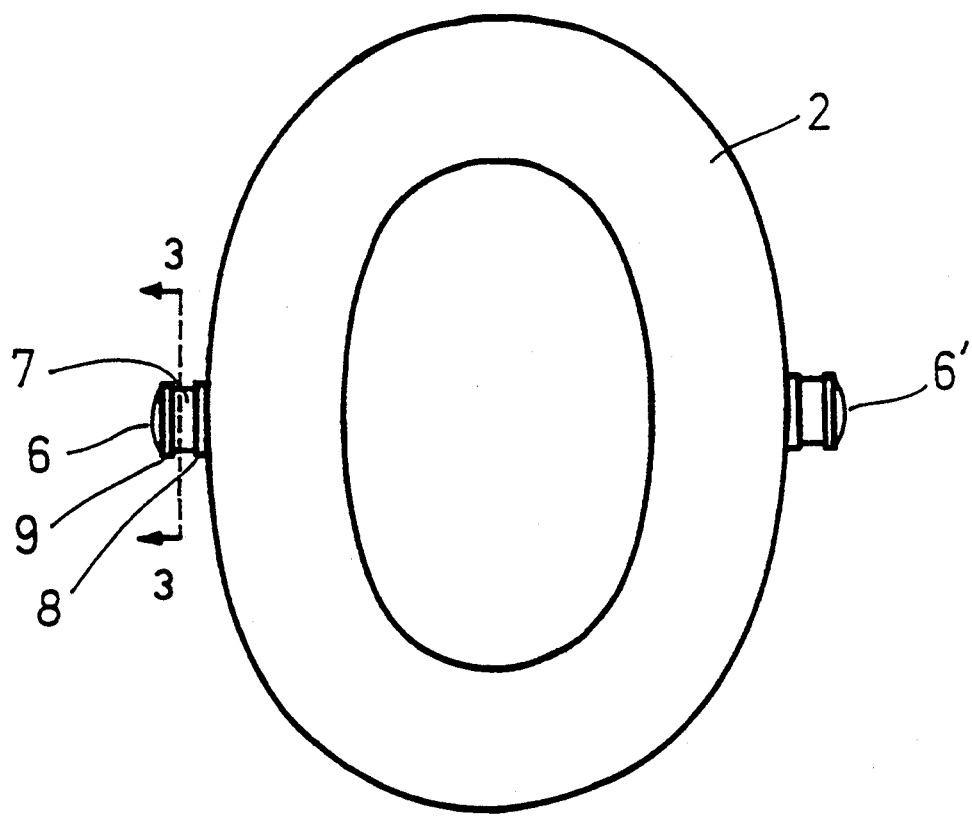
FIG. 2 shows one of the hearing-protection cups in FIG. 1 with two lateral sliding pins, seen in the direction of the cup opening.

Each ear defender cup 2, 2' is provided at the centre of its two outer longitudinal sides with a sliding pin for detachable attachment in a jaw element 5 pertaining to one of the four jaw sockets. Of these only sockets 4, 4' are shown in FIG. 1 and only the sliding pins 6, 6' are shown in Figure 2. The design and function of only one of the four identical snap-in members formed in this way will be explained in the following, that is to say the snap-in member formed by the jaw element 5 and pertaining to the socket 4, and the sliding pin 6.

Figures 3, 4:
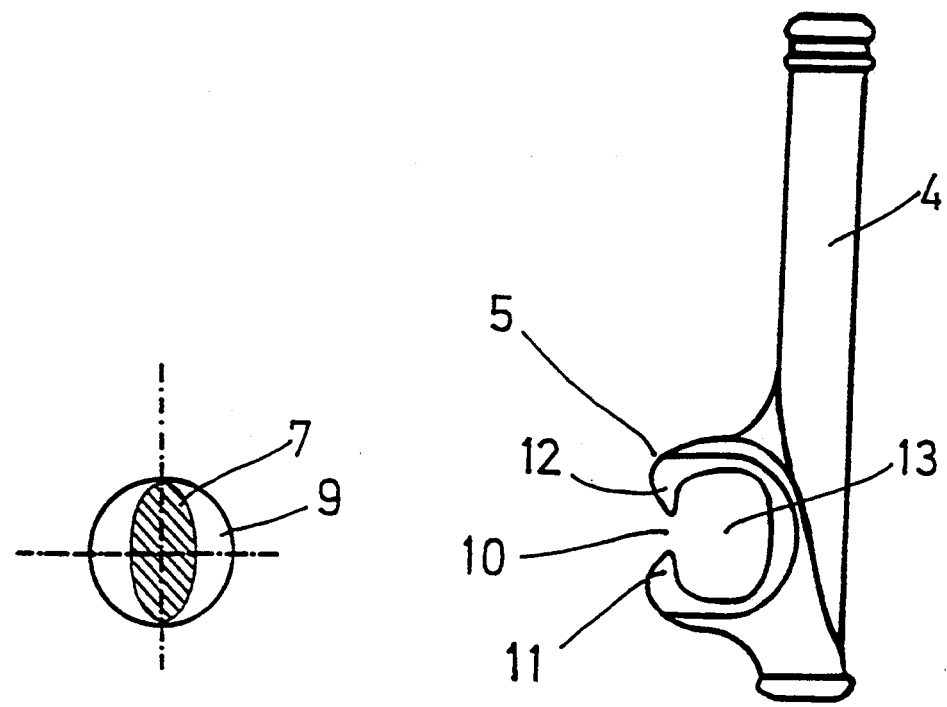
FIG. 3 shows one of the sliding pins along section 3—3 in FIG. 2, on an enlarged scale.
FIG. 4 shows a jaw member of an attachment according to the invention shown in FIG. 1, seen in side view and on an enlarged scale.

The sliding pin 6 made of polypropylene has a central journal section 7 with elliptical cross section, as shown in FIG. 3. The ratio between the length of the axes of the ellipse is 2:1. In axial direction the journal section 7 is limited by two annular flanges having a diameter somewhat larger than the longitudinal axis of the ellipse, an inner annular flange 8 and an outer annular flange 9. The longitudinal axis of the ellipse is thus substantially parallel to the surface of the cup 2 in contact with the wearer's head. The same orientation also applies to the other sliding pin on the opposite side of the cup.

Two jaws, a lower jaw 11 close to the free end of the socket 4 and an upper jaw 12 spaced from the lower jaw 11 in the direction of the headband 1 and forming a gap 10, extend from the jaw element 5 made of acetal plastic in a plane (the jaw plane) that also includes the longitudinal axis of the jaw socket 4. The width of the jaws 11, 12 perpendicular to the jaw plane is negligibly less than the width of the journal section 7, i.e. the distance between the annular flanges 8 and 9.

The gap 10 between the jaws 11, 12 expands towards a central cavity 14 (into which the end section of the frame 3 can slide) in the jaw socket 4, forming a locking space 13 with mirror-image symmetry about a symmetry axis S intersecting the gap 10 between the jaws 11, 12 and located perpendicular to the socket cavity, 14. Besides being open towards the gap 10, the locking space 13 is also open in a direction vertical to the jaw plane, its dimension in this direction being determined by the width of the jaw. A peripheral contact surface, only one of which 17 is shown, connects on each side to the two edges defining the inner wall 16 of the locking space. The contact surfaces 17, also comprising the side walls of the jaws 11, 12, are limited radially on both sides by U-shaped wall surfaces, only one wall surface 18 being shown, the legs of which open in the same direction as the gap 10, are parallel to the symmetry axis S of the locking space 13 and arranged symmetrically in relation thereto. The inner wall 16, contact surfaces 17 and wall surface 18 are designed to cooperate with the journal section 7 of the sliding pin 6 and lateral and radial surfaces of the annular flanges 8 and 9.

When being assembled the cup 2 is brought into a position in which one of its sliding pins 6 assumes the position in relation to the jaws 11, 12 shown in FIG. 6a, i.e. the longitudinal axis of the ellipse coinciding with the symmetry axis S as indicated by the broken line 15 in FIG. 6a (the limit line for the annular flanges 8 and 9), the ends of the jaws I 1 and 12 being inserted between the annular flanges 8 and 9 and abutting the journal section 7. When the journal section 7 is pressed against the jaws 11, 12 they are forced apart due to the wedge action of the ellipse and allow most of the journal section 7 to pass between them until the insertion end 19 of the journal section 7 abuts the rear wall 20 of the locking space 13. The snap-in contact has thus reached its first assembled stable position (inspection position), as shown in FIG. 6b. By turning the cup 2 and thus the journal section 7 about its axis—the insertion end 19 of the journal section 7 maintaining contact with the rear wall 20, but being displaced downwardly along this—the first end position (FIG. 6c) for the second stable position (operative position) of the snap-in contact is reached.

The centre of the journal section 7 now coincides with the centre of the locking space 13 and the longitudinal axis of the journal section 7 assumes an angle α of approximately 60° in relation to the symmetry axis S. Turning the cup 2 with journal section 7 further in clockwise direction until the second end position (FIG. 6d) has been reached requires no force since the circle-segment shaped wall portions 21 and 22 are defined by a radius of equal length or negligibly larger than the longitudinal axis of the ellipse defining the journal section 7. In the present case the angle β for the sector with free pivotability is approximately 60°, i.e. +30° from the normal N. In the position defined by the normal N the flat sides of the cups provided with openings will be parallel with each other. In order to obtain the two-step effect according to the invention the curvature of the rear wall section 20 must be considerably less than that of the wall sections 21 and 22. In the present case it is approximately half as great.

Assembly of the other snap-in connections, not shown, of the cups 2 and 2' is performed in corresponding manner. Of course all journal sections 7 will be inserted with the correct end to achieve symmetry of the cups when the two hearing-protection cups 2, 2' are assembled.

Upon transition through the configurations of the snap-in contact 7 shown in FIG. 6a–6c, the jaws 11, 12 are elastomerically deformed, whereupon the deformation in the first stable position shown in FIG. 6b is not reduced to zero but is decreased in relation to the maximum deformation upon transition through the configurations shown in FIGS. 1 and 2 and in FIGS. 2 and 3. Deformation occurs primarily in the outer parts of the jaws 11, 12 in a main direction indicated by the arrows D in FIG. 6a.

We claim:

1. In a detachable snap-in attachment for a headband or other support means for an ear defender cup which, when in place, is pivotable in relation to the headband, said snap-in attachment comprising:
   at least one sliding pin arranged on each of first and second opposite lateral sides of the ear defender cup in line with each other and perpendicular to the respective side;
   jaw elements at each end of the headband, each jaw element including a pair of jaws defining a gap, said jaw elements being arranged parallel to each other and symmetrically in relation to the sliding pins;
   stop flanges at the ends of each said pin so that, when in place in a recess defined by a respective one of said jaw elements, each sliding pin is held pivotably between the two jaws;
   the improvement wherein each of said sliding pins includes an axis of rotation and a journal section of non-circular cross-section taken in a plane perpendicular to said axis of rotation, with said cross-section having double mirror-image symmetry, and wherein to effect attachment of the ear defender cup to the headband or other support means the sliding pins can be inserted into the gap between the jaws only in the direction of the longitudinal axis of the journal section.

2. A snap-in attachment according to claim 1 wherein said non-circular cross-section is substantially oval or elliptical and said journal section is between said stop flanges.

3. A snap-in attachment as claimed in claim 2, wherein the ratio between the length of the minor axis of the non-circular cross section and its major axis is between substantially 1:1.3 and substantially 1:5.

4. A snap-in attachment as claimed in claim 3, wherein said ratio is substantially 1:2.

5. A snap-in attachment as claimed in claim 1, wherein, when in place, the sliding pins are freely pivotable in relation to the headband within an a sector whose sector angle is between substantially 20° and substantially 80°.

6. A snap-in attachment as claimed in claim 3, wherein said sector angle is substantially 55°.

7. A snap-in attachment as claimed in claim 1, wherein, when in place, the sliding pins are freely pivotable in relation to the headband within an angular range from the direction of insertion of the sliding pin in the gap between the jaws of from between substantially 50° and substantially 130° to between substantially 80° and substantially 100°.

8. A snap-in attachment according to claim 7, wherein said angular range is between substantially 62.5° and 107.5°.

9. A snap-in attachment as claimed in claim 1, wherein when in place the sliding pins are lockable in said jaw elements either in or transverse to the direction of insertion.

10. A snap-in attachment as claimed in claim 1, wherein each of the journal sections of a respective pivot pin enters an individual one of the recesses during attachment of the ear defender cup to the jaw element, said recess being defined by first and second opposite side walls, the first side wall of said first and second opposite side walls has an opening therein provided by the gap between said jaws and through which gap the journal section of the pin is inserted into said recess, and third and fourth opposite wall sections joining said first and second wall sections, wherein said third and fourth wall sections occupy a circular sector starting from between 40° and 75° relative to the direction of insertion measuring from the center of the recess along the direction of insertion of said journal section, of said pin between said jaws and ending at from 105° to 140° relative to said direction of insertion.

11. A snap-in attachment according to claim 10, wherein said sector extends between approximately 60° and 120° relative to said direction of insertion.

12. A snap-in attachment as claimed in claim 10, wherein the second side wall of said first and second opposite side walls has an inner surface shaped substantially as a segment of a circle facing the insertion gap and is defined by a first radius considerably larger than a second radius defining the circular sector defining said third and fourth opposite wall sections, said second side wall extending as a sector whose sector angle is substantially determined by angles of the circular sectors that are occupied by the third and fourth opposite wall sections.

13. A snap-in attachment as claimed in claim 12, wherein the first radius is approximately twice the second radius.

14. A snap-in attachment as claimed in claim 1, wherein the journal sections of the sliding pins are each insertable and lockable between the pair of jaws by being rotated to abut a first resilient counter member and are lockable in the recess by being rotated towards a second resilient counter member.

15. A snap-in attachment as claimed in claim 1, wherein the surfaces of the jaws able to abut the sliding pin and the surfaces of the sliding pin able to abut the jaws are shaped congruently.

16. A snap-in attachment as claimed in claim 15, wherein congruency between abutting surfaces of the sliding pin and the jaw is perpendicular to the plane of the jaws and parallel to said plane of the jaw, respectively.

17. An ear defender cup having at least one snap-in attachment defined in claim 1.

18. An ear defender unit having at least one snap-in attachment as defined in claim 1.

19. A noise-suppressed headset having at least one snap-in attachment as defined in claim 1.

20. A snap-in attachment according to claim 1 in which the sliding pins have diad axes of symmetry.

* * * * *